(12) United States Patent
Matsumoto et al.

(10) Patent No.: US 6,830,889 B1
(45) Date of Patent: Dec. 14, 2004

(54) METHOD OF DETECTING DNA BY DNA HYBRIDIZATION METHOD WITH THE USE OF FLUORESCENT RESONANCE ENERGY TRANSFER

(75) Inventors: Kazuko Matsumoto, Tokyo (JP); Shinji Sueda, Toda (JP)

(73) Assignee: Japan Science and Technology Agency, Saitama (JP)

( * ) Notice: Subject to any disclaimer, the term of this patent is extended or adjusted under 35 U.S.C. 154(b) by 0 days.

(21) Appl. No.: 10/181,826

(22) PCT Filed: Jul. 26, 2000

(86) PCT No.: PCT/JP00/04975
§ 371 (c)(1),
(2), (4) Date: Jul. 22, 2002

(87) PCT Pub. No.: WO01/53527
PCT Pub. Date: Jul. 26, 2001

(30) Foreign Application Priority Data

Jan. 20, 2000 (JP) ........................................ 2000-011771

(51) Int. Cl.⁷ ........................... C12Q 1/68; C12P 19/34; C07H 21/02; C07H 21/04
(52) U.S. Cl. .......................... 435/6; 435/91.1; 435/183; 435/287.2; 536/23.1; 536/24.3; 536/24.33; 436/94; 436/172; 436/800
(58) Field of Search ........................... 435/6, 91.1, 183, 435/287.2; 436/94, 172, 800; 536/23.1, 24.3, 24.33; 562/828, 833; 549/43, 57, 64; 558/13; 534/15, 16; 568/326

(56) References Cited

U.S. PATENT DOCUMENTS 5,556,959 A * 9/1996 Brush et al. ............. 536/25.32
5,859,297 A * 1/1999 Matsumoto et al. ........ 562/828
6,080,868 A * 6/2000 Lee et al. .................. 548/100

FOREIGN PATENT DOCUMENTS

WO          WO 99/39203     * 8/1999      ......... G01N/33/533

OTHER PUBLICATIONS

The Stratagene Catalog, p. 39 (1988).*
Shinji Sueda et al., "Homogenous Identification of DNA by Using Europium Fluorescence Energy Transfer," Department of Chemistry, School of Science and Engineering, Waseda University, Japan. 26$^{th}$ International Conference on Solution Chemistry, Jul. 26–32, 1999, Fukuoka, Japan (Program and Abstract).
Shinji Sueda et al., "Homogenous Identification of DNA by Using Europium Fluorescence Energy Transfer," Department of Chemistry, School of Science and Engineering, Waseda University, Japan. IUPAC 8$^{th}$ International Symposium on Macromolecule–Metal Complexes (MMC–8 Tokyo), Sep. 5–8, 1999, Waseda University, Tokyo (Program and Abstract).

* cited by examiner

*Primary Examiner*—Bradley L. Sisson
(74) *Attorney, Agent, or Firm*—Peter F. Corless; John B. Alexander; Edwards & Angell, LLP (57) ABSTRACT

A practically usable DNA detection method by a DNA hybridization method with the use of fluorescent resonance energy transfer wherein the background luminescence based on the luminescence of a donor and the direct excitation of an acceptor) affecting the sensitized luminescence of the acceptor is minimized so that a target DNA strand can be conveniently and very easily detected in a homogeneous solution. In this DNA detection method, a DNA is detected by the DNA hybridization method by using, as detection reagents, streptoavidin labeled with a fluorescent rare earth metal complex, a nucleic acid probe modified with biotin and a nucleic acid probe labeled with an organic cyanine pigment and taking advantage of florescent resonance energy transfer.

8 Claims, 6 Drawing Sheets

FIG. 1

31mer 5' CTGTTTCATGACGCAGATACCAGTGCTAGGTC 3' (SEQ ID No 4)
32mer 5' CTGTTTCATGACGCAGAGTACCAGTGCTAGGTC 3' (SEQ ID No 5)
33mer 5' CTGTTTCATGACGCAGAGTTACCAGTGCTAGGTC 3' (SEQ ID No 6)
34mer 5' CTGTTTCATGACGCAGAGTGTACCAGTGCTAGGTC 3' (SEQ ID No 7)

SEQUENCE LISTING

<160> NUMBER OF SEQ ID NOS: 7

<210> SEQ ID NO 1
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gacctagcac tggta                                                        15

<210> SEQ ID NO 2
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
ctgcgtcatg aacag                                                        15

<210> SEQ ID NO 3
<211> LENGTH: 31

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ctggatcgtg accatagacg cagtacttgt c                                     31

<210> SEQ ID NO 4
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
ctgttcatga cgcagatacc agtgctaggt c                                     31

<210> SEQ ID NO 5
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
ctgttcatga cgcagagtac cagtgctagg tc                                    32

<210> SEQ ID NO 6
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ctgttcatga cgcagagtta ccagtgctag gtc                                   33

<210> SEQ ID NO 7
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
ctgttcatga cgcagagtgt accagtgcta ggtc                                  34
```

METHOD OF DETECTING DNA BY DNA HYBRIDIZATION METHOD WITH THE USE OF FLUORESCENT RESONANCE ENERGY TRANSFER

TECHNICAL FIELD

The present invention relates to a method of detecting DNA by DNA hybridization method with the use of fluorescent resonance energy transfer and reagents used therefor.

BACKGROUND ART

A DNA hybridization method has been widely utilized for diagnoses of genetic and infectious diseases. Most conventional methods for target DNA detection based on the DNA hybridization method are time-consuming and troublesome because they require many procedures such as immobilization of the target DNA on the solid support and washing of hybridized DNA duplex from the excess probe DNA. A method for detecting DNA based on fluorescence resonance energy transfer (FRET) has been proposed as a method to avoid these problems. That is, it is the method to detect DNA in a homogenous solution by preparing two nucleic acid probes (DNA probes) labeled with compounds to be an energy donor and an acceptor at the terminus and utilizing resonance energy transfer (sensitized luminescence of the acceptor) induced when these two nucleic acid probes (DNA probes) bind to the target DNA.

However, because organic dyes have been primarily utilized as the energy donor and the acceptor in conventional systems, a background luminescence (luminescence based on luminescence of the donor and the direct excitation of the acceptor) affecting a sensitized luminescence of the acceptor is significantly large resulting in no report of a practical system applicable for target DNA detection.

DISCLOSURE OF THE INVENTION

In the lights of the above circumstance, the objective of the present invention is to provide a practically usable method for detecting DNA by a DNA hybridization method with the use of fluorescent resonance energy transfer wherein the background luminescence (i.e., luminescence based on the luminescence of a donor and the direct excitation of an acceptor) affecting the sensitized luminescence of the acceptor is minimized so that a target DNA duplex can be conveniently and very easily detected in a homogenous solution.

The present invention relates to (1) a method for detecting DNA by the DNA hybridization method using as detection reagents, streptoavidin labeled with a fluorescent rare earth metal complex, a nucleic acid probe modified with biotin and a nucleic acid probe labeled with an organic cyanine dye, and taking advantage of fluorescent resonance energy transfer.

Also, the present invention relates to (2) a method for detecting DNA by the DNA hybridization method using a fluorescent rare earth metal complex as an energy donor, using an organic cyanine dye as an acceptor and taking advantage of fluorescent resonance energy transfer.

Further, the present invention relates to (3) a nucleic acid probe labeled with a fluorescent rare earth metal complex via biotin-streptoavidin.

Still, the present invention relates to a reagent kit comprising a nucleic acid probe modified with biotin, a nucleic acid probe modified with an organic cyanine dye and streptoavidin labeled with a fluorescent rare earth metal complex.

Still further, the present invention relates to (4) a reagent kit comprising a nucleic acid probe modified with biotin, a nucleic acid probe modified with a compound represented by the following chemical formula (II), and streptoavidin labeled with 4,4'-bis(1",1",1",2",2",3",3"-heptafluoro-4",6"-hexanedione-6"-yl)-chlorosulfo-o-terphenyl (BHHCT)/Eu³⁺complex:

(II)

(wherein MMTO represents 4-monomethoxytrityl group.)

Also, the present invention relates to (5) reagents for the method for detecting DNA by the DNA hybridization method taking advantage of fluorescent resonance energy transfer, comprising streptoavidin labeled with a fluorescent rare earth metal complex.

Further, the present invention relates to (6) a process for producing the nucleic acid probe described in the above (3), characterized in that the nucleic acid probe modified with biotin and the nucleic acid probe modified with the organic cyanine dye are mixed with a sample containing a target DNA, hybridized, and subsequently reacted with streptoavidin labeled with the fluorescent rare earth metal complex.

And also, the present invention relates to a method for detecting a target DNA by mixing a sample containing the DNA with a nucleic acid probe modified with biotin and a nucleic acid probe modified with an organic cyanine dye followed by hybridizing, then reacting streptoavidin labeled with a fluorescent rare earth metal complex therewith to further introduce the fluorescent rare earth metal complex, and subsequently measuring fluorescence of the DNA duplex.

BEST MODE FOR CARRYING OUT THE INVENTION

The representatives of the fluorescent rare earth metal complex used in the present invention include lanthanide complex. The lanthanide complex is a complex of a lantern lineage element of which atomic number is from 57 to 71, and those of which luminescence has been observed are the complexes of 4 types of elements, Eu, Tb, Sm and Dy. Among them, europium (Eu) and terbium (Th) are included as the preferred ones. Among them, a quadridentate coordination β diketone type europium complex, a complex of trivalent europium (Eu$^{3+}$is especially preferable in the present invention. The specific example includes 4,4'-bis(1", 1",1",2",2",3",3"-heptafluoro as "BHHCT-Eu(III)" hereinafter) as the preferred one.

The structural formula of BHHCT is shown below.

Specific examples of Eu and Th complexes in addition to the above include, for example, DTPA-cs124 (diethylenetriamine pentaacetate-carbostyril 124) Eu complex (or Tb complex) represented by the chemical formula (III) and TBP (tris bipyridine) Eu complex (or Tb complex) represented by the chemical formula (IV):

(wherein Ln$^{3+}$ represents Eu$^{3+}$or Tb$^{3+}$; and)

(wherein Ln$^{3+}$is the same as defined above.)

The organic cyanine dyes used in the present invention include, for example, a compound represented by the following chemical formula (I):

wherein $R_1$ and $R_2$ represent substituents such as active ester groups and the like, and allophycocyanin (APC) which is dye protein, and the like. The representatives of the compounds represented by the chemical formula (I) include Cy5 (trademark of Amersham Pharmacia Biotech Ltd.). The structural formula of Cy5 is as shown in the above chemical formula, and various substituents such as active ester groups and the like are introduced to $R_1$ and $R_2$. Also, those to which sulfonic acid group (—SO$_3^-$) is introduced and not introduced are included. The dyes with such structures are collectively referred to Cy5 (trademark of Arnersham Pharmacia Biotech Ltd.). The representative of Cy5 used in the present invention includes Cy5 phosphoroamidite represented by the above chemical formula (II).

For a process for preparing streptoavidin labeled with the fluorescent rare earth metal complex, when the fluorescent rare earth metal complex is BHHCT-Eu(III) complex, the preparation ca be carried out according to the method described, for example, in Anal. Biochem., 254:283–287 (1997) and the like. That is, first, streptoavidin is dissolved in a buffer such as carbonate buffer, BHHCT dissolved in dry ethanol is added thereto, then stirred to react, and subsequently unreacted BHHCT is removed by conducting dialysis. Then, when this is reacted with $EuCl_3$, for example, in tris-hydrochloride buffer, the objective streptoavidin labeled with BHHCT-Eu (III) can be readily obtained.

For a process for preparing various modified nucleic acid (DNA) probes (modified DNA oligonucleotide) used in the present invention, it is enough to prepare according to the methods for the preparation of nucleic acid probes (DNA probes) known in the art. That is, any synthesis of oligonucleotides can be carried out by the phosphoroamidite method using an automatic DNA synthesizer, and purification can be carried out using a reverse phase HPLC. Also, the introduction of biotin and the organic dye can be carried out according to the standard methods using, for example, a biotinylated agent such as biotin TEG phosphoroamide (supplied by Glen Research) and the like and a dye derivative such as Cy5 phosphoroamidite (supplied by Glen Research) and the like, respectively.

Figure 1:
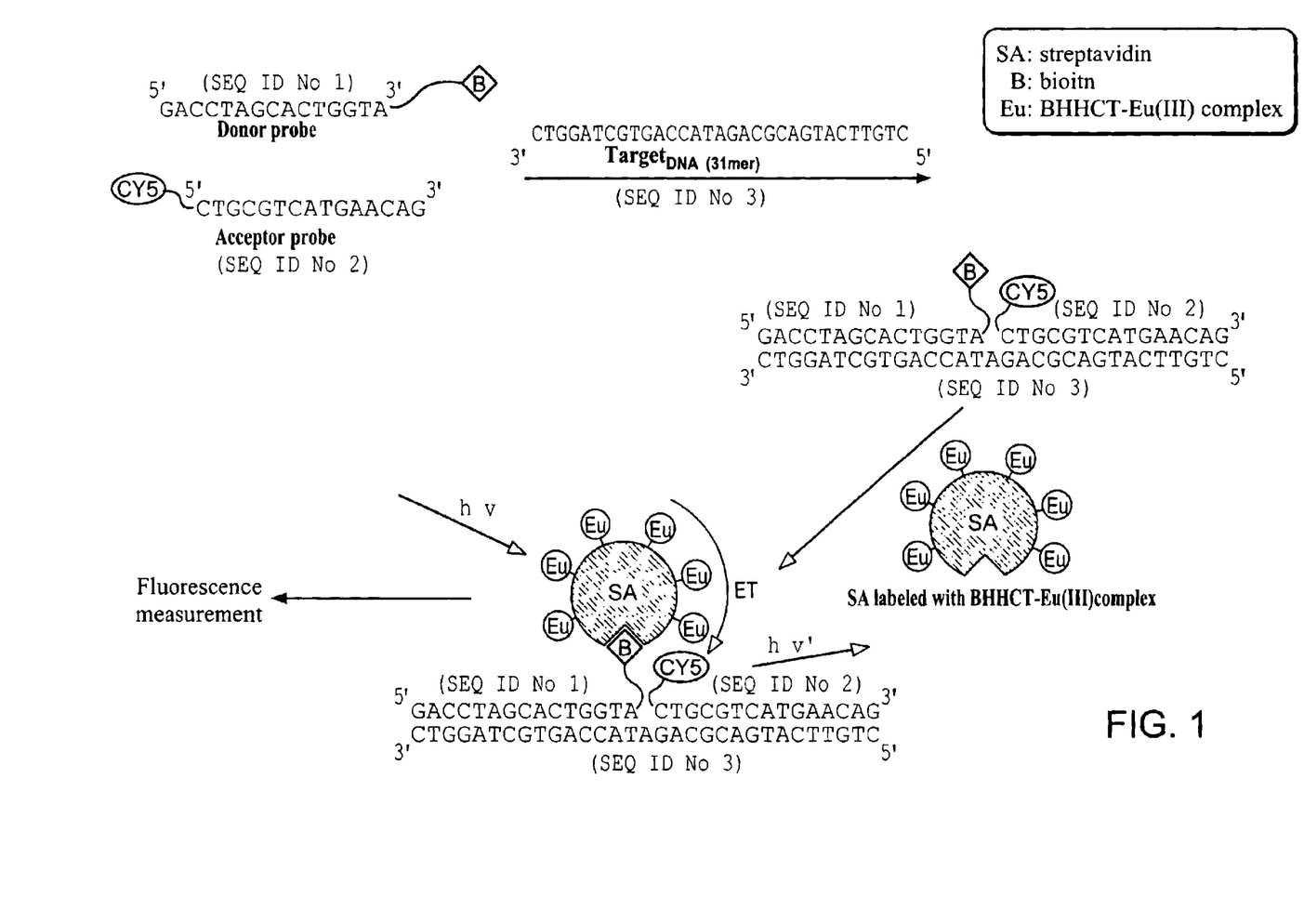
FIG. 1 (SEQ ID NOS 1–3) schematically represents the detection method of the present invention in the case of using 4,4'-bis(1",1",1",2",2",3",3"-heptafluoro-4",6"-hexanedione-6"-yl)-chlorosulfo-o-terphenyl (BHHCT)Eu³⁺ complex as the fluorescent rare earth metal complex and using Cy5 as the organic cyanine dye.

The present invention relates to the method for detecting/determining DNA by the hybridization method using the fluorescent rare earth metal complex (e.g., BHHCT-Eu (III) complex) as the energy donor and the organic cyanine dye (e.g., Cy5) as the acceptor and taking advantage of fluorescent resonance energy transfer, and is characterized in that streptoavidin labeled with the fluorescent rare earth metal complex (e.g., BHHCT-Eu (III), the nucleic acid probe modified with biotin and the nucleic acid probe labeled with the organic cyanine dye (e.g., Cy5) are used as the reagents for detection and determination. The process for the determination of the present invention is shown in FIG. 1 wherein the case where BHHCT-EU (III) complex and Cy5 are used as the fluorescent rare earth metal complex and the cyanine organic dye, respectively is schematically represented.

That is, first, the DNA probe introduced biotin at the 3' end and the DNA probe introduced Cy5 at the 5' end are prepared. These probes are designed to be capable of proximately existing one another when hybridized with their target DNA. After hybridizing with the target DNA, streptoavidin labeled with Eu (III) complex (SA) is added, and fluorescent determination is carried out. In this case, only when two DNA probes is hybridized with their target DNA, energy transfer can occur in principle from BHHCT-Eu (III) complex to Cy5, resulting in observing a luminescent band of Cy5. Therefore, it enables to simply detect the target DNA in a homogenous solution (without washing/eliminating the excess DNA probes and labeled SA) by monitoring a luminescent intensity of Cy5.

In the present determination system, Eu (III) complex was introduced into the DNA oligonucleotide which become the probe by utilizing an interaction of biotin-streptoavidin. That is, the oligonuclcotide introduced biotin at the terminus was prepared, and streptoavidin labeled with Eu (III) complex (SA) was interacted therewith resulting in introducing Eu (III) complex into the oligonucleotide. This aims to make Cy5 emit effectively by increasing a modification rate of Eu (III) complex per probe and to save the trouble of labeling Eu (III) complex for each objective (having a base sequence) DNA probe (oligonucleotides modified with biotin can be readily prepared using an automatic DNA synthesizer).

The detection method of the present invention may be carried out by the method measuring fixed light excitation luminescence or by the method for the time resolved fluorescent detection. Any types of fluorescent spectrometers usually used can be used for the detection of fluorescence.

Avidin, instead of streptoavidin, can be used in the method and for the reagents of the present invention (but, in this case, a background luminescence possibly becomes larger).

In the present invention, the nucleic acid probe modified with biotin and the nucleic acid probe modified with Cy5 are hybridized with the target DNA, and subsequently streptoavidin labeled with Eu (III) complex is reacted therewith. However, it is possible that first, streptoavidin labeled with Eu (III) complex is reacted with the biotin introduced nucleic acid probe, and that subsequently it is hybridized with the target DNA (but, streptoavidin is a protein with molecular weight of about 60,000 which is much larger than the oligonucleotide of about 15-mer and thus it is possible that hybridization of the oligonucleotide might be prevented in the condition where such a huge protein is bound to the terminus).

EXAMPLES

Next, the present invention is more particularly described by examples, but the invention is not limited to these examples and specific descriptions.

Example 1

Labeling Streptoavidin with BHHCT and Formation of Complex with Eu (III))

Streptoavidin (5 mg) (SA) was dissolved in 33 ml of 0.1M carbonate buffer (pH 9.1), 0.2 ml of dry ethanol containing 4 mg of BHHCT (synthesized according to the method described in Anal. Chem., 70:597–598, 1998) was added thereto over 5 min, and subsequently stirred at room temperature for one hour to conduct a modification. Thereafter, unreacted BHHCT was eliminated by performing dialysis and purification was carried out. The modification rate of BHHCT to SA was about 20 molecules.

Complexation with Eu (III) was carried out by adding equivalent molar $EuCl_3$ to BHHCT in 50 mM Tris-HCl buffer (pH 7.8) followed by leaving at 55° C. for 2 hours.

Example 2

Preparation of Modified DNA Oligonucleotide and Target DNA oligonucleotide

Figure 2:
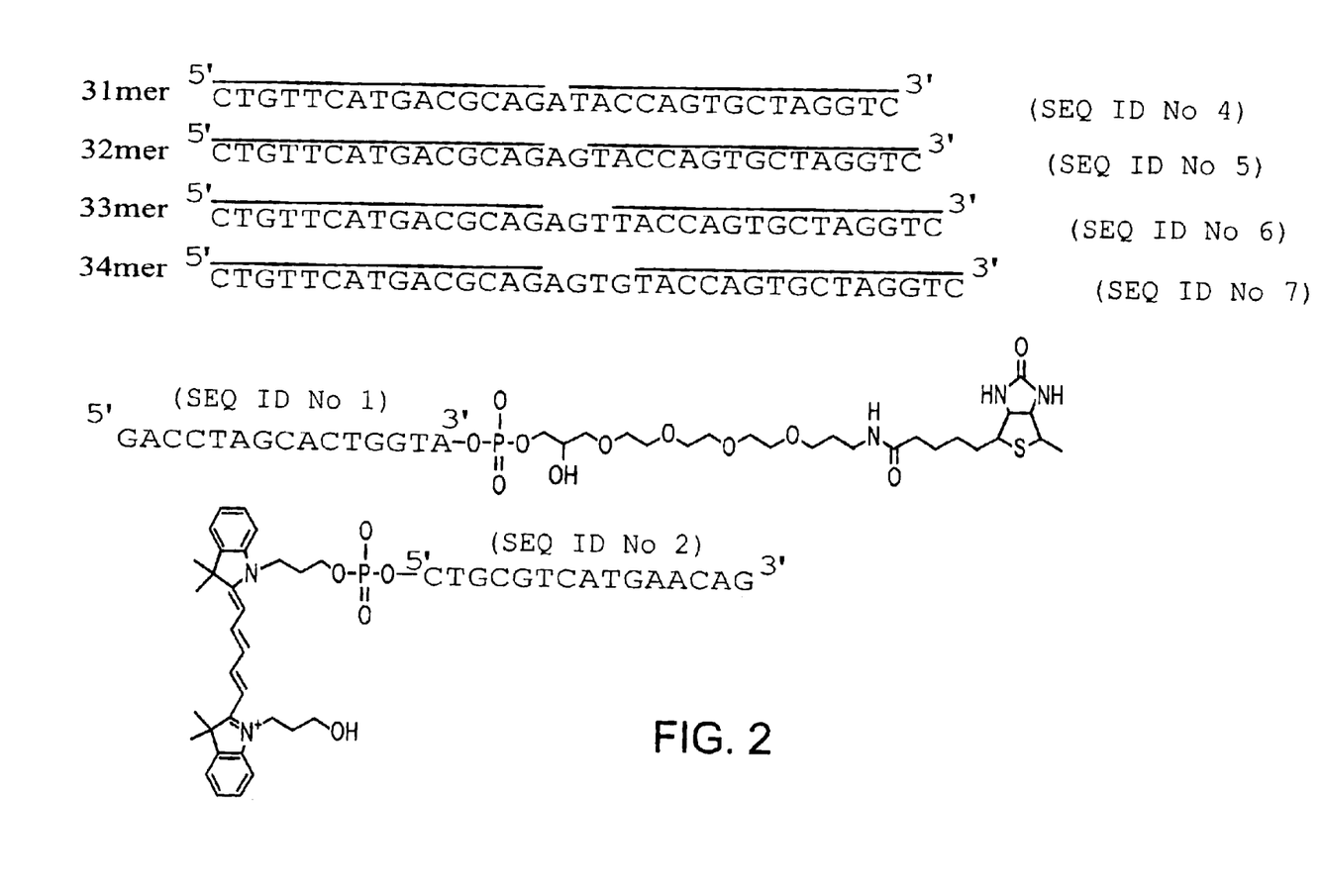
FIG. 2 (SEQ ID NOS 4–7 and 1–2 respectively) shows the target oligonucleotides, and biotin- and Cy5-modified oligonucleotides used in the examples.

FIG. 2 shows the modified DNA oligonucleotide and the DNA oligonucleotide to become a target used in the present invention. All oligonucleotides were synthesized by the phosphoroamidite method using an automatic DNA synthesizer. The purification was carried out by a reverse phase HPLC. Biotin TEG phosphoroamide (supplied by Glen Research) and Cy5 phosphoroamidite (supplied by Glen Research) were used for the introduction of biotin into the 3' end and of Cy into the 5' end, respectively.

Example 3

Hybridization of the DNA Oligonucleotides

Hybridization was carried out by mixing 0.5 μM of the biotin modified oligonucleotide, 0.5 μM of the Cy5 modified oligonucleotide and the target oligonucleotide at a given concentration in 10 mM Tris-Hcl buffer (pH7.8) containing 0.5 M of Nacl and heating for 15 min followed by cooling back to room temperature over 1 to 2 hours.

Example 4

Detection of Fluorescence

A solution of standardized SA containing equivalent molar SA molecules to the biotinylated DNA probe was added to a solution of the hybridized DNA, left at room temperature for one hour, and subsequently fluorescence was detected. At that time, NaCl was added to the solution to control such that the NaCl concentration of the solution was 0.5M. All cases of fluorescence detection employed LS 50B luminescence spectrometer (Perkin-Elmer).

Properties of Spectra

Figure 3:
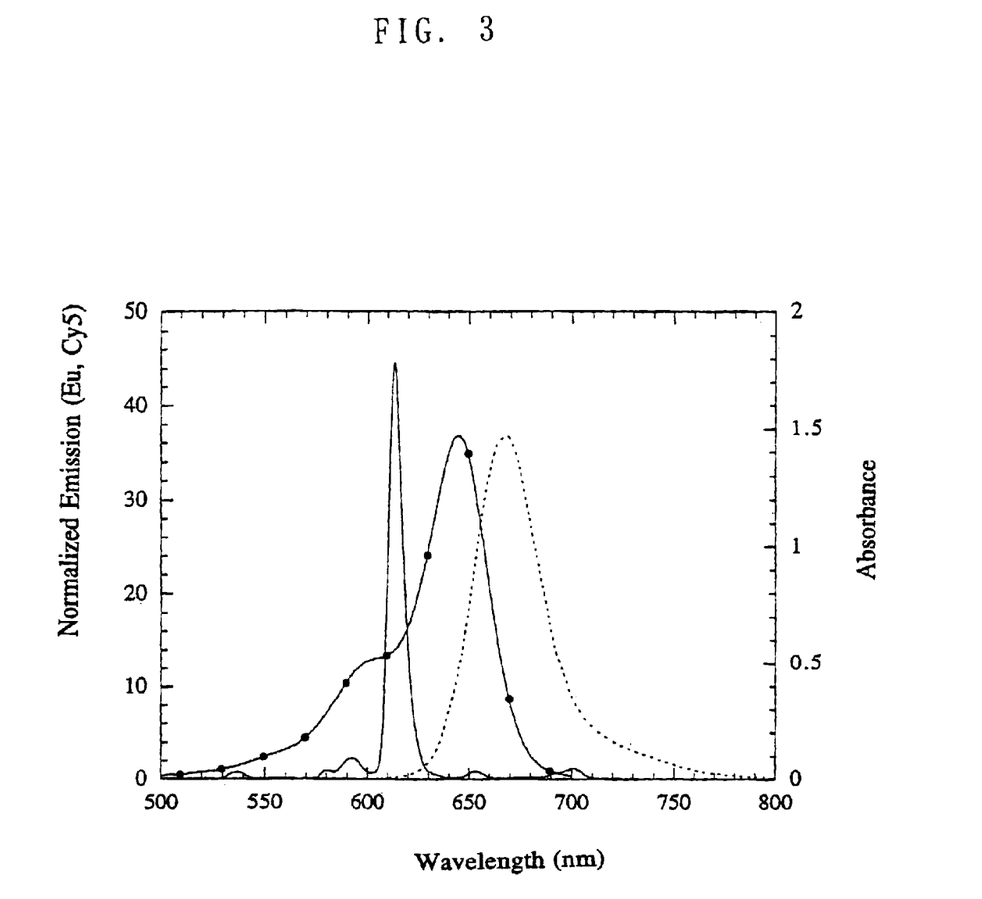
FIG. 3 shows a fluorescent luminescent spectrum of the Eu (III) complex bound to streptoavidin (SA)($\lambda_{ex}$=340 nm) (solid line), a fluorescent luminescent spectrum of the Cy5-modified oligonucleotide ($\lambda_{ex}$=643 nm)(dot line), and an absorption spectrum (solid line with closed circles).

FIG. 3 shows the spectrum of fluorescent luminescence of Eu (III) complex bound to streptoavidin (SA), and the spectra of fluorescent luminescence and absorption of the Cy5 modified oligonucleotide. It has been demonstrated in some previous studies that the sensitized emission of Cy5 is induced by the luminescence of Eu (III). Here, it is remarkably notable that the degree of luminescence of BHHCT-Eu(III) complex is extremely small at 669 nm which is the maximum luminescent wavelength of Cy5 (the luminescent intensity of Eu (III) complex at 669 nm is $1/280$ of that at 614 nm). This indicates that it is possible to minimize a background effect based on the luminescence of Eu (III) complex upon the observation for sensitized luminescence of Cy5.

Study on Energy Transfer

Figure 4:
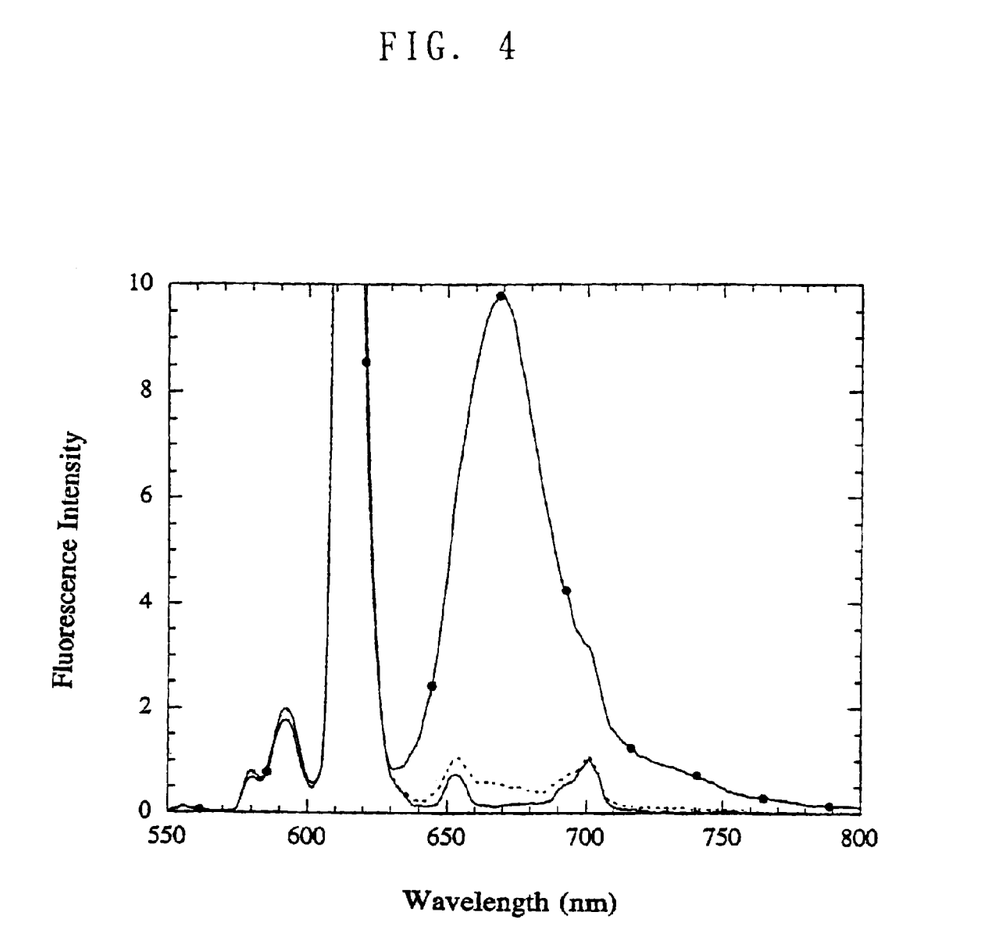
FIG. 4 shows fixed light excitation luminescent spectra in the presence (solid line with closed circles) or absence (dot line) of the target DNA (31-mer), and a fluorescent luminescent spectrum of Eu (III) complex alone bound to SA measured under the same condition (solid line).

FIG. 4 shows the spectra of fixed light excitation luminescence in the presence or absence of the target DNA (31-mer)(the concentrations of the biotin modified DNA probe, the Cy5 modified DNA probe and the target DNA were all 50 nM. Excitation wavelength $\lambda_{ex}$=340 nm). The luminescent band of Cy5 mainly at 669 nm became larger by adding the target DNA. This indicates that an effective energy transfer occurred only when the target DNA was present. FIG. 4 also shows the spectrum of fluorescent luminescence of Eu (III) complex alone which was bound to SA determined under the same condition. When this spectrum of fluorescence (solid line) is compared with the spectrum of fluorescence in the absence of the target DNA (dot line), some Cy5 luminescent bands can be observed in the latter spectrum. These some Cy5 luminescent bands are based on direct excitation of Cy5 (see the discussion for the time resolved spectra described below). However, since this luminescent intensity is considerably smaller than the intensity of sensitized luminescence of Cy5, resulting in a considerably high ratio of signal to background of 18:1 at 669 nm. It is impossible to obtain such a high ratio of signal to background in the case of using a common organic dye donor/acceptor pair.

Figure 5:
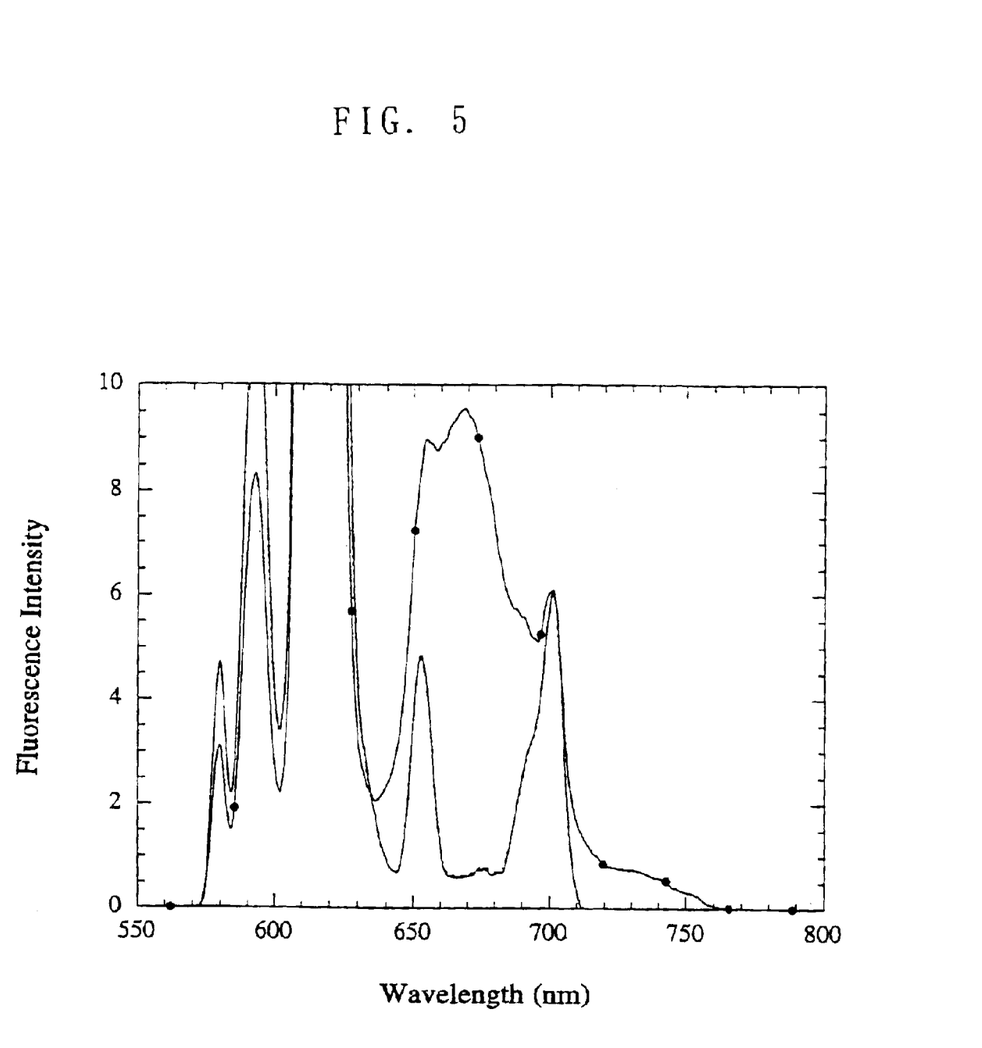
FIG. 5 shows time resolved fluorescent luminescent spectra in the presence (solid line with closed circles) or absence (dot line) of the target DNA (31-mer), and the time resolved fluorescent luminescent spectrum of Eu (III) complex alone bound to SA (solid line).

The similar study was carried out by the time resolved fluorescent detection method. FIG. 5 shows the spectra of the time resolved fluorescence obtained (the concentrations of the biotin modified DNA probe, the Cy5 modified DNA probe and the target DNA were all 50 nM. Excitation wavelength $\lambda_{ex}$=340 nm). As is the case with the fixed light excitation spectra, the Cy5 luminescent bands were increased by adding the target DNA (31-mer). However, it has been found that when the luminescent spectrum (solid line) of Eu (III) complex alone which were bound to SA is compared with the spectrum (dot line) in the absence of the target DNA, both are almost completely identical. This indicates that the luminescent band of Cy5 (based on direct excitation) observed in the absence of the target DNA in FIG. 4 disappears by conducting the time resolving fluorescent detection. On the other hand, in this case, the luminescent intensity of Eu (III) complex became relatively larger to the sensitized luminescent intensity of Cy5 (due to relatively longer lifetime of Eu (III) luminescence compared to that of the sensitized luminescence of Cy5), resulting in a similar level of the ratio of signal to background as in the case of the fixed light excitation. As mentioned above, this level of the signal to background ratio is obviously more excellent compared to the systems reported previously.

Effect of the Number of Bases Between the Target Sequences of the DNA Probes The effect of the base number present between the sequences targeted by two DNA probes on the target DNA was examined. For this purpose, 31-mer, 32-mer, 33-mer and 34-mer were prepared of which base numbers between the target sequences were 1, 2, 3 and 4, respectively. The intensity of the sensitized luminescence of Cy5 was observed with co-existence of the respective target DNA. Table 1 together shows relative values of the luminescence intensity of Cy5 at 669 nm in the case of each target DNA.

TABLE 1

Comparison of the relative luminescent intensity at 669 nm

| | Relative luminescent intensity |
|---|---|
| 31-mer | 1.00 |
| 32-mer | 0.96 |
| 33-mer | 0.95 |
| 34-mer | 0.93 |

*Used was the data of the fixed light excitation fluorescent spectra at the concentration of 50 nM for DNA probes and target DNA.

As obviously from Table 1, as the base number was increased between the target sequences, the luminescence intensity was observed to have a tendency to be decreased as expected. However, the extent of this decrease is only 10% even when one base is compared to four bases, and it is an extremely small value, considering that efficiency of energy transfer depends on R" (R: distance between the donor and acceptor). This seems to be ascribed to that Eu (III) complex which is the donor labels multiple molecules (about 20 molecules) through SA but not modify at a single molecule of the end of the DNA probe, and that biotin is introduced at the end of the oligonucleotide via a long linker.

This is an extremely advantageous for designing the probes. The reason is that it is not necessary to introduce an absolutely defined number of bases between the target DNA sequences to obtain high efficiency of energy transfer, leading to flexibility of probe design.

Sensitivity of the Present Detection

Figure 6:
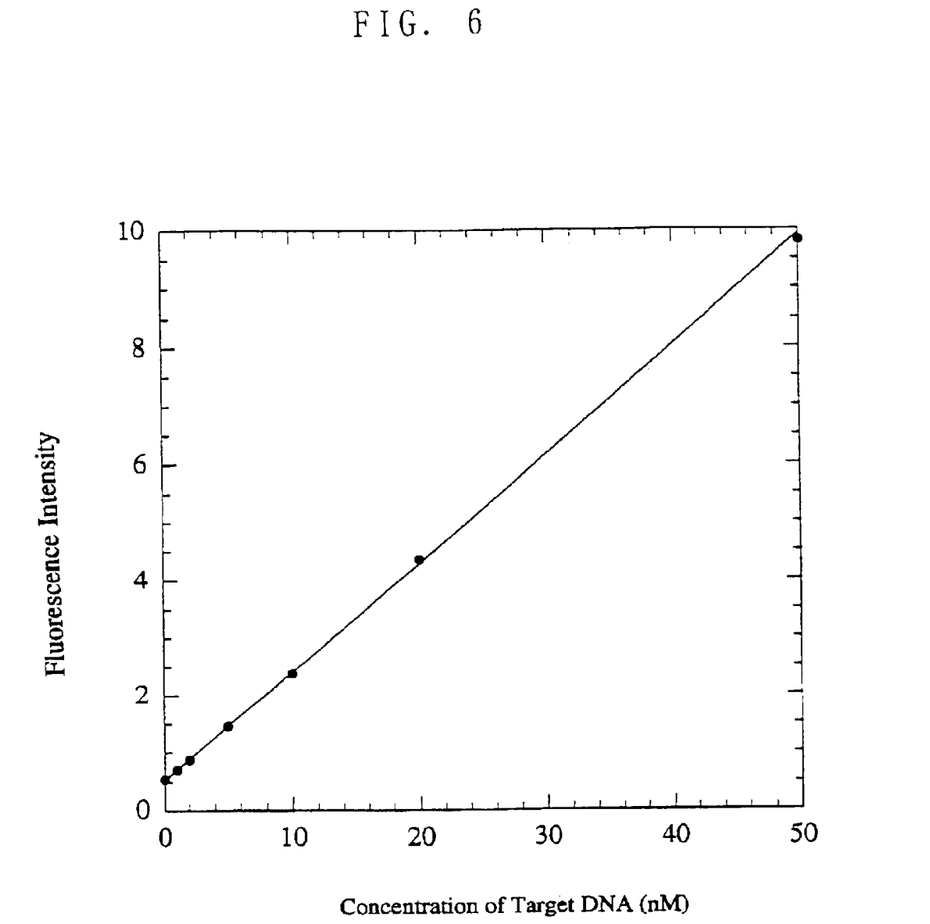
FIG. 6 shows a change of the luminescent intensity at 669 nm depending on a concentration change of the target DNA (31-mer)(excitation wavelength $\lambda_{ex}$=340 nm).

Sensitivity of the present detection was examined using 31-mer as the target DNA. FIG. 6 shows those plotting the change of the luminescent intensity of Cy5 at 669 nm with the concentration change of the target DNA (31-mer)(used are the data of the fixed light excitation fluorescence detection at the concentration of 50 nM for the DNA probes). This plot is based on the result of the fixed light excitation fluorescence detection, and the similar result was obtained from the case of the time resolved fluorescence detection. The detection limit was about 200 $\mu$M in both detection methods when calculated with [background emission +2×standard deviation] in the condition using 50 nM of the DNA probe. It seems to be possible that the detection level might be lowered using the DNA probe at a lower concentration.

There is no difference of the detection limit between the fixed light excitation fluorescence detection and the time resolved fluorescence detection in the present detection system using the synthetic oligonucleotide as the target DNA. However, in the case of detecting actual samples with contaminants, the time resolved fluorescence detection appears to be more advantageous since it can eliminate the background emission based on the contaminants.

INDUSTRIAL APPLICABILITY

The present invention is to provide the technique to detect the DNA duplex in the homogenous solution utilizing the fluorescent rare earth metal complex of which representative is BHHCT-Eu (III) complex as the energy donor and the organic dye of which representative is Cy5 as the acceptor, and the advantages of the present detection method are as follows.

(1) The background signal which affects the sensitized luminescence of the acceptor is smaller compared to conventional systems using the organic dye donor/acceptor pair.

One reason is that the emission of BHHCT-Eu (III) complex is extremely small at 669 nm which is the maximum emission wavelength of Cy5 in the case of using BHHCT-Eu (III) complex as the energy donor and Cy5 as the acceptor. Another reason is that the time resolved fluorescence detection can eliminate the luminescence based on direct excitation of the acceptor. For this luminescence based on direct excitation of the acceptor, it is possible to minimize the emission even in the common fixed light excitation fluorescence detection without conducting the time resolved fluorescence detection. This is due to the extremely low excitation efficiency of Cy5 at 340 nm which is the excitation wavelength of Eu (III) complex (the absorptivity, $\epsilon$ of Cy5 at 340 nm is about $1/70$ of $\epsilon$ at 643 nm). Therefore, the present detection system is characterized in that the similar signal/background ratio can be obtained as that in the time resolved fluorescence detection without conducting the time resolved fluorescence detection.

(2) Effective emission of the organic dye with extremely large absorptivity, e.g., Cy5 can be obtained because Eu (III) complex is indirectly introduced into the DNA probe utilizing the interaction of streptoavidin (SA) and biotin.

Eu (III) complex used in the present invention is the complex emitting the strongest fluorescence among Eu (III) complexes capable of being standardized reported previously ($\epsilon_{340}$=30000, quantum yield 1=0.25). However, since the absorptivity, $\epsilon$ of Cy5 is 200000 or more at 643 nm, a single molecule of Eu (III) complex is insufficient to obtain effective emission of Cy5. Thus, in the present invention, about 20 molecules of Eu (III) complex were served for one molecule of Cy5 by modifying Eu (III) complex to SA. This enabled the extremely large sensitized luminescence of Cy5 (about a half fluorescent intensity of the case directly exciting Cy5 at 643 nm utilizing the identical fluorescence spectrometer having Xe lamp).

(3) The step where each Eu (III) complex is labeled for each DNA probe having the target base sequence can be saved because Eu (III) complex is indirectly introduced into the DNA probe utilizing the interaction of streptoavidin (SA) and biotin.

That is, since the biotin modified oligonucleotides can be readily prepared using an automatic DNA synthesizer, DNA probes corresponding to various sequences can be readily prepared only with the preparation of SA labeled with Eu (III) complex.

(4) Since high efficiency of energy transfer is obtained by utilizing necessary to always introduce the defined number of the bases sequences resulting in flexibility for design of probes. As mentioned above, the present detection method has some novel advantages, and can be referred to the first practical detection system in which DNA duplex can be detected in the homogenous solution by taking advantage of energy transfer.

What is claimed is:

1. A method for detecting DNA in a sample comprising carrying out the following processes defined in steps (1) and (2) or in steps (3) or (4):
   (1) hybridizing to the DNA contained in the sample a biotin-modified nucleic acid probe and a nucleic acid probe labeled with an organic cyanine dye which is sensitized to luminescence by fluorescent resonance energy transfer, and
   (2) binding streptavidin labeled with 4,4'-bis (1",1",2",2",3",3"-heptafluoro-4",6"-hexanedione-6"-yl)-chlorosulfo-o-terphenyl (BHHCT)/Eu3+ complex to the biotin in the DNA duplex obtained by above (1), or
   (3) binding streptavidin labeled with 4,4"-bis-(1",1",2",2",3",3"-heptafluoro-4",6"-hexanedione-6"-yl)-chlorosulfo-o-terphenyl (BHHCT)/Eu3+ complex to the biotin in a biotin-modified nucleic acid probe, and
   (4) hybridizing to the DNA contained in the sample the probe obtained by above (3) and a nucleic acid probe labeled with an organic cyanine dye which is sensitized to luminescencence by fluorescent resonance energy transfer; and
   detecting and measuring the fluorescent resonance energy transfer luminescence spectrum of the organic cyanine dye.

2. The method according to claim 1, wherein the organic ding to chemical formula (I);

(I)

(wherein R1 and R2 represent substituents such as active ester groups and the like.)

3. The method according to claim 2, wherein the organic cyanine chemical formula (II):

(II)

(wherein MMTO represents 4-momomethoxytrityl group.)

4. A method for detecting DNA based on fluorescence resonance energy transfer, wherein the method is characterized by using 4,4-bis (1",1",1",2",2",3",3"-heptafluoro-4", 6"-hexanedione-6"-yl)-chlorosulfo-o-terphenyl (BHHCT)/Eu$^{3+}$ complex as an energy donor and an organic cyanine dye according to chemical formula (II):

(II)

(wherein MMTO represents 4-monomethoxytrityl group) as an acceptor, and measuring fluorescence of the acceptor due to fluorescent resonance energy transfer.

5. A method for detecting DNA in a sample comprising by mixing and hybridizing the DNA to a biotin-modified nucleic acid probe and a nucleic acid probe modified with an organic cyanine dye according to chemical formula (I):

(wherein $R_1$ and $R_2$ represent substituents such as active ester groups and (—$SO_3^-$) means, that the site is substituted by —$SO_3^-$ or unsubstituted), reacting steptoavidin labeled with 4,4'-bis (1",1",1",2",2", 3",3"-heptafluoro-4",6'-hexanedione -6"-yl)-chloro-sulfo-o-terphenyl (BHHCT)/Eu$^{3+}$ complex therewith to further introduce (BHHCT)/Eu$^{3+}$complex and measuring fluorescence of the DNA duplex.

6. Reagents for detecting DNA based on fluorescent resonance energy transfer, comprising streptavidin labeled with 4,4'-bis(1",1",1",2",2",3",3"-heptafluoro -4",6"-hexanedione-6"-yl)-chlorosulfo-o-terphenyl (BHHCT)Eu$^{3+}$ complex.

7. A reagent kit comprising a nucleic acid probe modified with biotin, a nucleic acid probe modified with an organic cyanine dye according to chemical formula (I):

(I)

(wherein $R_1$ and $R_2$ represent substituents such as active ester groups and (—$SO_3^-$) means that the site is substituted by —$SO_3^-$ or unsubstituted);

and streptavidin labeled with 4,4'-bis (1",1",1",2",2",3",3"-heptafluoro-4",6"-hexanedione-4",6"-hexanedione-6"-yl)-chlorosulfo-o-terphenyl (BHHCT)/Eu$^{3+}$ complex.

8. The reagent kit according to claim 7, wherein the organic cyanine dye is a compound according to chemical formula (II):

(II)

(wherein MMTO represents 4-monomethoxytrityl group).

* * * * *